United States Patent [19]

Morgan et al.

[11] 4,060,603
[45] Nov. 29, 1977

[54] HISTIDINE DERIVATIVES
[75] Inventors: Barry A. Morgan, Hull; Derek J. Schafer, Harpenden, both of England
[73] Assignee: Reckitt & Colman Products Limited, London, England
[21] Appl. No.: 659,913
[22] Filed: Feb. 20, 1976
[30] Foreign Application Priority Data
　　Mar. 8, 1975　United Kingdom ............... 10144/75
[51] Int. Cl.$^2$ ..................... A61K 37/00; C07C 103/52
[52] U.S. Cl. ........................... 424/177; 260/112.5 TR
[58] Field of Search ............... 260/112.5 TR; 424/177
[56]　　　　　References Cited
U.S. PATENT DOCUMENTS 3,931,139　1/1976　Wissmann et al. ......... 260/112.5 TR
3,959,248　5/1976　Veber et al. ............... 260/112.5 TR Primary Examiner—Delbert R. Phillips
Attorney, Agent, or Firm—Bacon & Thomas

[57]　　　　　ABSTRACT

Compounds of the formula

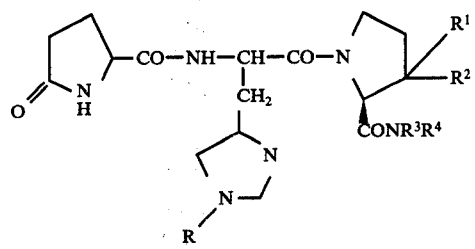

wherein R, $R^1$, $R^2$, $R^3$ and $R^4$ represent certain specified substituent groups. The compounds exhibit activity in the reserpine induced hypothermia test.

14 Claims, No Drawings

HISTIDINE DERIVATIVES

This invention relates to histidine derivatives, to processes for their preparation, and to therapeutic compositions thereof.

According to this invention there are provided compounds of the formula I:

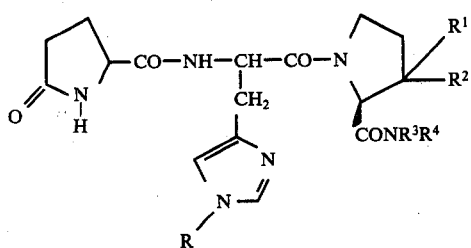

wherein R is hydrogen or alkyl $C_{1-3}$, $R^1$ is alkyl or alkoxy $C_{1-3}$; $R^2$ is hydrogen, alkyl or alkoxy $C_{1-3}$; $R^3$ is hydrogen, alkyl $C_{1-6}$, or cycloalkyl $C_{3-6}$; and $R^4$ is hydrogen or alkyl $C_{1-6}$.

The compounds are derived from the amino-acids, L-pyroglutamic acid and L-histidine and it is to be understood that in the compounds of formula I the histidyl and pyroglutamyl residues are in the L-configuration.

The invention also provides therapeutic compositions comprising a compound of formula I, in association with a pharmaceutically acceptable diluent or carrier.

The compounds of the invention exhibit pharmacological activity in mice in the reserpine hypothermia method, a test to screen for anti-depressant activity, and may be expected to be of use in the treatment of depression. The compounds being chemically related to the hypothalamic thyrotropin releasing hormone (TRH), L-pyroglutamyl-L-histidyl-L-prolineamide, may be expected to exhibit similar effects on the pituitary gland.

The compounds of the invention may be prepared by coupling a L-histidine derivative of formula II

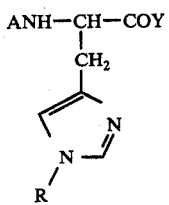

wherein A and Y are respectively either protecting groups or groups capable of forming peptide linkages with firstly either

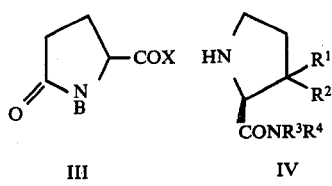

a. a compound of formula III wherein B is hydrogen or a protecting group and X is a group capable of forming peptide linkage; or
b. a compound of formula IV and secondly the resultant dipeptide is coupled with the other compound, and removing any protecting groups.

Conveniently the compounds may be prepared by coupling by the standard techniques of peptide chemistry a compound of formula II wherein R is as hereinbefore defined, A is hydrogen and Y is a protecting group such as a lower alkoxy group $C_{1-4}$, with a compound of formula III wherein X is a group capable of forming a peptide linkage such as hydroxy, substituted phenoxy (e.g. p-nitrophenoxy, tri- or penta-chlorophenoxy) or azido and B is hydrogen or a protecting group such as benzyloxycarbonyl to form a dipeptide group in which thereinafter the group Y is converted to a group capable of forming the peptide linkage such as hydroxy or azido, and reacted with a compound of formula IV wherein $R^1$, $R^2$, $R^3$ and $R^4$ are as hereinbefore defined, with subsequent removal of any protecting groups. Coupling reaction involving a carboxyl group i.e. in formula II when X is hydroxy or in the dipeptide when Y is hydroxy are carried out in the presence of a coupling agent such as N, N'-dicyclohexylcarbodiimide, preferably in the presence of a racemisation inhibitor such as hydroxybenzotriazole.

Alternatively the compounds may be prepared by coupling by the standard techniques of peptide chemistry a compound of formula II wherein R is as hereinbefore defined, A is a N-protecting group commonly used in peptide chemistry (such as t-butoxycarbonyl or benzyloxycarbonyl), and Y is a group capable of forming a peptide linkage such as hydroxy, substituted phenoxy, or azido with a compound of formula IV wherein $R^1$, $R^2$, $R^3$ and $R^4$ are as hereinbefore defined to form a dipeptide. The N-protecting group is removed and the resultant compound coupled by standard methods of peptide chemistry with a compound of formula III wherein X is a group capable of forming a peptide linkage such as hydroxy, substituted phenoxy, azido or chlorine and B is hydrogen or a protecting group such as benzyloxycarbonyl, with subsequent removal of any protecting groups. Coupling reactions involving free carboxy groups i.e. when X or Y are hydroxy are carried out in the presence of a coupling agent such as N, N'dicyclohexylcarbodiimide preferably in the presence of a racemisation inhibitor such as hydroxybenzotriazole.

The compounds of formula IV wherein $R^1$, $R^2$, $R^3$ and $R^4$ are as hereinbefore defined may be prepared from the corresponding alkyl substituted prolines by protecting the imino function with for example t-butoxycarbonyl or benzyloxycarbonyl groups, activating the carbonyl group by one of the standard methods of peptide chemistry (such as the mixed anhydride or activated ester method), coupling the activated compound with ammonia or an amine in a suitable solvent and removing the N-protecting group by standard methods of peptide chemistry.

This invention is illustrated by the following non-limiting Examples in which the temperatures are in degrees centigrade.

EXAMPLE 1

L-Pyroglutamyl-L-histidyl-trans-3-methyl-L-prolineamide (I, R = H, $R^1$ = trans—3—$CH_3$, $R^2$ = $R^3$ = $R^4$ = H)

i. N-t-Butoxycarbonyl-trans-3-methyl-L-proline
Triethylamine (3.5 ml) and t-butyl-2,4,5-trichlorophenyl carbonate (3.5 g) were added to a solution of trans- 3-methyl-L-proline (1.25 g) in t-butanol (12 ml) and water (8 ml). The mixture was heated to 60° for 2 hours, evaporated, the residue dissolved in 1 N sodium bicarbonate solution (50 ml) and the solution washed with ether. Excess solid citric acid was added, the product extracted into ethyl acetate, the combined extracts dried (Na$_2$SO$_4$) and evaporated giving a crude crystalline product (1.6 g). Recrystallisation from ethyl acetate/light petroleum (40°-60°) gave the desired product (1.33 g), m.p. 146°-150° [α]$_D^{20}$ − 60.1° (c, 1.0, chloroform)

ii. N-t-Butoxycarbonyl-trans-3-methyl-L-prolineamide

N-Methyl morpholine (6.0 ml) was added to a solution of N-t-butoxy-carbonyl-trans-3-methyl-L-proline (1.1 g) in tetrahydrofuran (50 ml) at −20°. Freshly distilled isobutylchloroformate (0.8 g) was added dropwise and the solution stirred for 10 minutes at −20°. Concentrated ammonia solution (5 ml) was added and the solution stirred for 2 hours, evaporated, the residue taken up in ethyl acetate (100 ml) and the solution washed with 10% aqueous sodium bicarbonate, brine and dried (Na$_2$SO$_4$). Evaporation gave the crude crystalline product (1.0 g). Recrystallisation from ethyl acetate/light petroleum (40°-60°) gave the desired product (0.91 g) m.p. 100°-101°, [α]$_D^{20}$ −79.7° (c, 1.0, chloroform)

iii. trans-3-Methyl-L-prolineamide-hydrochloride

A solution of hydrogen chloride in dioxan (7.5 N, 5 ml) was added to a solution of N-t-butoxycarbonyl-trans-3-methyl-L-prolineamide (0.65 g) in 10 ml dioxan. After 2 hours the crystalline solid was filtered and recrystallised from ethanol/ether to give the product (0.47 g), m.p. 235°-237° [α]$_D^{20}$ −14.8° (c, 1.0, water).

iv. L-Pyroglutamyl-L-histidyl-trans-3-methyl-L-prolineamide trans-3-Methyl-L-prolineamide hydrochloride (0.50 g) in dimethylformamide (5 ml) was added to a solution of L-pyroglutamyl-L-histidine azide, prepared from the hydrazide (0.9 g), in dimethylformamide (15 ml) at −20°, and triethylamine (0.45 ml) added. The mixture was left at room temperature for 12 hours, filtered, evaporated, the residue dissolved in 1% aqueous pyridine (10 ml) and applied to a colunm of sulphoethyl "Sephadex" C-25 resin (50 g weighted as moist resin; 2 cm column diameter) equilibrated with 1% aqueous pyridine.

The column was eluted by a gradient technique using 5% aqueous pyridine via a 1 l spherical mixing vessel filled with 1% aqueous pyridine. The fractions containing product (as detected by optical rotation and t.l.c.) were combined, evaporated, and the residue triturated with ether giving the product (as the monohydrate) as an amorphous solid (0.70 g). [α]$_D^{20}$ − 46.7° (c, 1.0, water). R$_F$3B 0.48 m.p. 145°-148°

Analysis

Found C, 52.5 : H, 7.0 : N, 21.3 C$_{17}$H$_{24}$N$_6$O$_4$, H$_2$O requires C, 51.8 : H, 6.7 : N, 21.3%

EXAMPLE 2

L-Pyroglutamyl-L-histidyl-trans-3-ethyl-dl-prolineamide i. trans-3-ethyl-dl-proline Diethyl benzyloxycarbonylaminomalonate (11.5 g, 38 mM) was dissolved in dry ethanol (50 ml) and added to a solution of sodium (150 mg) in dry ethanol (10 ml). Pent-2-enal (3.2 g 38 mM) in ethanol (10 ml) was added dropwise to the stirred mixture and the solution stirred for 1 hr. A solution of acetic acid (0.29 ml) in ethanol (1 ml) was then added and the solution hydrogenated for 2 hrs at atmospheric pressure using palladium on carbon (5%) as catalyst. The catalyst was removed by filtration and the filtrate evaporated. The residue was dissolved in chloroform and the solution washed with brine containing a little sodium bicarbonate, dried (Na$_2$SO$_4$) and evaporated. Distillation of the residue at 15 mm Hg gave 4-ethyl-5,5-dicarboethoxy-2-pyrroline (5.65 g) as a colourless oil b.p. 115°-120° (15 mm Hg) I.R. 1715, 1610 cm$^{-1}$.

The pyrroline (4.68 g, 19.5 mM) was added to a mixture of 1M NaOH (80 ml) and ethanol (80 ml) and the solution stirred at 50° for 4 hrs. The solution was then cooled, sodium borohydride (1.0 g) added, and stirred at 25° for a further 10 hours. The solution was then carefully acidified with dilute HCl to pH 4, concentrated and applied to a column of Dowex 50WX8 resin (H+ form, 100 ml) Elution with aqueous ammonia (2 M) yielded a solution which on evaporation gave trans-3-ethyl-dl-proline (2.1 g) m.p. 208-209°; R$_F$3B 0.43. Analysis on a Jeol 6AH amino acid analyser (50 cm column, sodium citrate buffer 0.2 N, pH 3.25 temperature 57°) showed a single peak (elution time 117 mins).

ii. t-Butyloxycarbonyl-trans-3-ethyl-dl-proline

This was prepared from trans-3-ethyl-dl-proline (1.72 g) by the method of example 1(i) as an oil (2.82 g) R$_F$3A 0.92 iii. t-Butyloxycarbonyl-trans-3-ethyl-dl-prolineamide

This was prepared from t-butyloxycarbonyl-trans-3-ethyl-dl-proline (3.5 g) by the method of Example 1(ii) to yield, after chromatography on a silica column t-butyloxycarbonyl-trans-3-ethyl-dl-prolineamide (3.1 g) as white crystals m.p. 78°-80°;

iv. trans-3-Ethyl-dl-prolineamide hydrochloride

This was prepared from t-butyloxycarbonyl-trans-3-ethyl-dl-prolineamide (3.0 g) by the method of Example 1(iii) to yield trans-3-ethyl-dl-prolineamide hydrochloride (1.5 g) as white crystals m.p. 206°-207° R$_F$3A 0.22 R$_F$3B 0.72.

v. trans-3-Ethyl-dl-prolineamide trans-3-Ethyl-dl-prolineamide hydrochloride (0.5 g) was dissolved in water and passed down a column of DEAE-Sephadex resin (OH$^-$ form). The fractions containing product (as detected by t.l.c.) were combined and evaporated to dryness to yield trans-3-ethyl-dl-prolineamide hydrate (0.45 g) as a white solid m.p. 89.5°-91° R$_F$3A 0.22 R$_F$3B 0.72 vi. L-Pyroglutamyl-L-histidyl-trans-3-ethyl-dl-prolineamide trans-3-Ethyl-dl-prolineamide (288 mg, 2 mM), benzyloxycarbonyl-L-pyroglutamyl-L-histidine (822 mg, 2 mM), and hydroxybenzotriazole (550 mg, 4 mM) were dissolved in dimethylformamide (6 ml), the solution cooled to 0°, dicyclohexylcarbodiimide (480 mg, 2.2 mM) added and the mixture stirred for 18 hrs. The mixture was then filtered and the filtrate evaporated. The resulting oil was dissolved in tetrahydrofuran - water (1 : 1, 80 ml), palladium on carbon (10%, 60 mg) added and the solution hydrogenated for 4 hrs at atmospheric pressure. The catalyst was then removed by filtration and the filtrate evaporated to dryness. The resulting gum was distributed between ethyl acetate (50 ml) and water (80 ml). The aqueous phase was separated, evaporated to dryness and the residue dissolved in aqueous solution containing 1% acetic acid/0.05% pyridine. This was applied to a column of S.P. - Sephadex C 25 resin (pyridinium form) which was equilibrated with aqueous 1% acetic/0.05% pyridine. The column was eluted by a gradient technique using aqueous 1% acetic acid/1% pyridine via a 500 ml spherical mixing vessel filled with aqueous 1% acetic acid/0.05% pyridine. The fractions containing product (as detected by t.l.c) were combined and evaporated to yield L-pyroglutamyl-L-histidyl-trans-3-ethyl-dl-prolineamide (205 mg) as a white amorphous solid m.p. 156°–160°. $R_F3A$ 0.27, $R_F3B$ 0.50. Amino acid analysis after acidic hydrolysis gave the following ratios: Histidine 0.95 glutamic acid 0.99 3-ethyl proline 1.06.

EXAMPLE 3

L-Pyroglutamyl-L-histidyl-3,3-dimethyl-dl-prolineamide i. 3,3-Dimethyl-dl-proline Diethyl benzyloxycarbonylaminomalonate (3.09 g, 10 mM) was dissolved in dry ethanol (15 ml) and added to a solution of sodium ethoxide (from 100 mg sodium) in ethanol (3 ml). 3-Methylbut-2-enal (840 mg, 10 mM) in ethanol (6 ml) was added and the solution stirred at 25° for 24 hrs. Acetic acid (0.28 ml) was then added and the solution hydrogenated for 24 hrs using palladium on carbon (10% 500 mg) as catalyst. The solution was filtered, evaporated and the residue chromatographed on silica column using ether/petroleum ether (40°–60°) (1 : 1) as eluant to give 2,2-dicarboethoxy-3,3-dimethyl-pyrrolidine (0.9 g).

This diester (850 mg) was refluxed in 5 M hydrochloric acid (10 ml) for 4 hrs to give, after evaporation, a powdery white solid. Recrystallisation from methanol-ether gave 3,3-dimethyl-dl-proline hydrochloride (451 mg) as white crystals m.p. 110°–112°.

ii. t-Butyloxycarbonyl-3,3-dimethyl-dl-proline

This was prepared from 3,3-dimethyl-dl-proline hydrochloride (1.07 g) by the method of Example 1(i) to yield t-butyloxycarbonyl-3,3-dimethyl-dl-proline (1.45 g) as a white crystalline solid m.p. 107°–108.5°.

iii. t-Butyloxycarbonyl-3,3-dimethyl-dl-prolineamide

This was prepared from t-butyloxycarbonyl 3,3-dimethyl-dl-proline (900 mg) by the method of Example 1(ii) to yield t-butyloxycarbonyl-3,3-dimethyl-dl-prolineamide (375 mg) was a white crystalline solid m.p. 115°–117°.

iv. 3,3-Dimethyl-dl-prolineamide hydrochloride

This was prepared from t-butyloxycarbonyl-3,3-dimethyl-dl-prolineamide (300 mg) by the method of Example 1(iii) to yield 3,3-dimethyl-dl-prolineamide hydrochloride (175 mg) as a white crystalline solid m.p. 220°–223° v. 3,3-Dimethyl-dl-prolineamide

This was prepared from the hydrochloride salt (170 mg) by the method of Example 2(v) as a white solid (135 mg) $R_F3A$ 0.19 $R_F3B$ 0.70.

vi. L-Pyroglutamyl-L-histidyl-3,3-dimethyl-dl-prolineamide

This was prepared from 3,3-dimethyl-dl-prolineamide (100 mg) by the method of Example 2(vi) as a white powder (195 mg) m.p. 180° (softening 135°) $R_F3B$ 0.65. Amino acid analysis after acid hydrolysis gave the following ratios: Histidine 1.02, Glutamic acid 0.89 3,3-dimethylproline 1.02 $[\alpha]_D^{22} + 5.9°$ ($c = 1$, dimethylformamide)

EXAMPLE 4

L-Pyroglytamyl-N$^\xi$-methyl-L-histidyl-trans-3-methyl-L-prolineamide i. Benzyloxycarbonyl-L-pyroglutamyl-N$^\xi$-methyl-L-histidine N$^\xi$-Methyl-L-histidine (428 mg) and sodium carbonate (288 mg) was dissolved in water (5 ml) and the solution adjusted to pH 8.5. Benzyloxycarbonyl-L-pyroglutamic acid N-hydroxsuccinimido ester (933 mg) in dioxane (5 ml) was added and the solution stirred for 15 hrs at 22°. The solution was evaporated and the residue chromatographed on a silica gel column (15 × 330 mm) using isopropanol-ethyl acetate - acetic acid - water (3 : 1 : 1 : 1) as eluant to give, after evaporation of the appropriate fraction, the product (615 mg) as a white solid m.p. 192°–195° $R_F3A$ 0.21 $R_F3B$ 0.69 $[\alpha]_D^{22}$ − 1.3° ($c = 1$, dimethylformamide)

ii. L-Pyroglutamyl-N$^\xi$-methyl-L-histidyl-trans-3-methyl-L-prolineamide

This was prepared from benzyloxycarbonyl-L-pyroglutamyl-N$^\alpha$-methyl-L-histidine (207 mg) and trans-3-methyl-L-prolineamide (77 mg) by the method of Example 2(vi) to yield a white hydroscopic solid (90 mg) $R_F3A$ m.p. 135°–140° $R_F3B$ 0.60 (Found C, 55.0; H, 7.0; N, 21.2; $C_{18}H_{23}N_6O_4$ requires C, 55.4; H, 6.7; N, 21.5%) $[\alpha]_D^{22}$ − 23.9° ($c = 1$, dimethylformamide).

EXAMPLE 5

L-Pyroglutamyl-L-histidyl-trans-3-methyl-L-prolinecyclohexylamide i. t-Butyloxycarbonyl-trans-3-methyl-L-prolinecyclohexylamide This was prepared from t-butyloxycarbonyl-trans-3-methyl-L-proline (1.15 g) and cyclohexylamine (2.85 ml) by the method of Example 1(ii) as a white solid (1.3 g) m.p. 130°–134° $R_F1F$ 0.53.

ii. Trans-3-methyl-L-prolinecyclohexylamide

This was prepared from t-butyloxycarbonyl-trans-3-methyl-L-prolinecyclohexylamide (900 mg) by the method of Examples 1(iii) and 1(iv) to yield a white solid (410 mg) m.p. 111°–113°. $R_F2A$ 0.33 iii. L-Pyroglutamyl-L-histidyl-trans-3-methyl-L-prolinecyclohexylamide

This was prepared from benzyloxycarbonyl L-pyroglutamyl-L-histidine (565 mg) and trans-3-methyl-L-prolinecyclohexylamide (300 mg) by the method of Example 2(vi) as a white solid (272 mg) m.p. 145°–150°. $R_F3A$ 0.43 $R_F3B$ 0.78 $[\alpha]_D^{22}$ − 14.9° ($c = 1$, dimethylformamide) $R_F4A$ 0.50

EXAMPLE 6

L-Pyroglutamyl-L-histidyl-trans-3-methyl-L-prolinehexylamide

This was prepared by the method of example 5 to yield a white powder $R_F4A$ 0.52 $R_F3B$ 0.82

In the above Examples thin layer chromatography (t.l.c.) was performed on Kieselgel $GF_{254}$ plates and using the following solvent systems:

1E Methanol, chloroform 1:4
1F Methanol, chloroform 1:9
2A Chloroform, methanol, acetic acid 18:2:1
3A Chloroform, methanol, acetic acid, water 80:18:2:3
3B Chloroform, methanol, acetic acid, water 30:20:4:6

4A n-Butanol, ethyl acetate, acetic acid, water 1:1:1:1
6C n-Butanol, pyridine, acetic acid, water 30:20:6:12
7C Ethyl acetate, pyridine, acetic acid, water 120:20:6:11

The compound of Example 1 when tested in mice in the reversal of reserpine induced hypothermia test according to the method of B. M. Askew, Life Sci., 10, 725, (1963) exhibited a significant (P < 0.05, Mann Whitney U test)calorigenic effect over 4 hours in fully reserpinised mice This compound was 3–4 time more potent than TRH when administered in doses 1–30 mg/Kg p.o.

The therapeutic compositions may be in a form suitable for oral administration or in a form suitable for parenteral administration. Such oral compositions may take the form of capsules, tablets, granules or liquid preparations such as elixirs, syrups or suspensions.

Compositions intended for parenteral administration may be in the form of sterile injectable preparations such as solutions in water or saline.

For the purposes of convenience of accuracy of dosing the compositions are advantageously employed in a unit dosage form. For oral administration the unit dosage form may contain from 1 mg to 100 mg of a compound of Formula I.

What is claimed is:

1. Compounds of the formula:

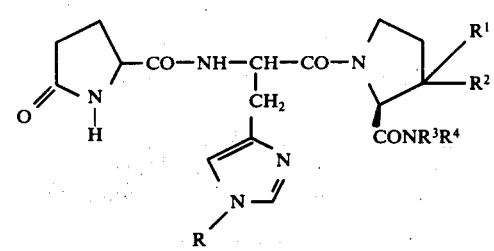

wherein R is hydrogen or alkyl $C_{1-3}$; $R^1$ is alkyl or alkoxy $C_{1-3}$; $R^2$ is hydrogen, alkyl or alkoxy $C_{1-3}$; $R^3$ is hydrogen, alkyl $C_{1-6}$, or cycloalkyl $C_{3-6}$; and $R^4$ is hydrogen or alkyl $C_{1-6}$.

2. Compounds of the formula:

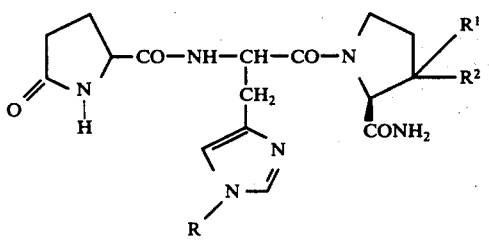

wherein R is hydrogen or alkyl $C_{1-3}$; $R^1$ is alkyl or alkoxy $C_{1-3}$; $R^2$ is hydrogen, alkyl or alkoxy $C_{1-3}$.

3. Compounds of the formula:

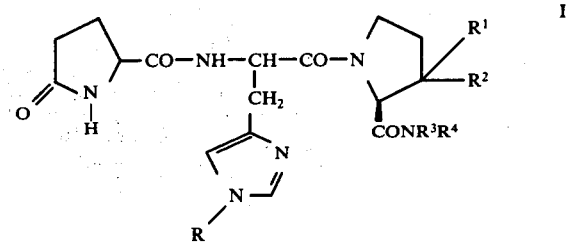

wherein R is hydrogen or alkyl $C_{1-3}$; $R^1$ is alkyl $C_{1-3}$; $R^2$ is hydrogen or alkyl $C_{1-3}$; $R^3$ is hydrogen, alkyl $C_{1-6}$, or cycloalkyl $C_{3-6}$; and $R^4$ is hydrogen or alkyl $C_{1-6}$.

4. A compound of Formula I as claimed in claim 3 wherein R is hydrogen or methyl; $R^1$ is methyl or ethyl; $R^2$ is hydrogen of methyl; $R^3$ is hydrogen, hexyl or cyclohexyl; and $R^4$ is hydrogen.

5. A pharmaceutical composition which comprises a compound of Formula I as claimed in claim 3 and a pharmaceutically acceptable diluent or carrier.

6. Compounds of the formula:

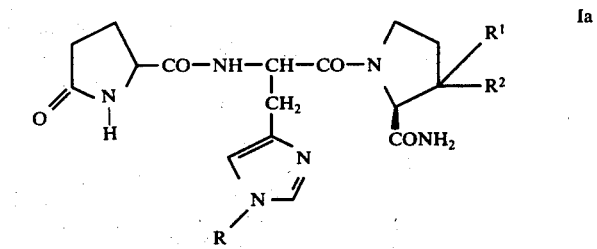

wherein R is hydrogen or alkyl $C_{1-3}$; $R^1$ is alkyl $C_{1-3}$; $R^2$ is hydrogen or alkyl $C_{1-3}$.

7. A compound of Formula Ia as claimed in claim 6 wherein R is hydrogen or methyl; $R^1$ is methyl or ethyl; and $R^2$ is hydrogen or methyl.

8. L-Pyroglutamyl-L-histidyl-trans-3-methyl-L-prolineamide.

9. L-Pyroglutamyl-L-histidyl-trans-3-ethyl-dl-prolineamide.

10. L-Pyroglutamyl-L-histidyl-3,3-dimethyl-dl-prolineamide.

11. L-Pyroglutamyl-N$^\alpha$-methyl-L-histidyl-trans-3-methyl-L-prolineamide.

12. L-Pyroglutamyl-L-histidyl-trans-3-methyl-L-prolinecyclohexylamide.

13. L-Pyroglutamyl-L-histidyl-trans-3-methyl-L-prolinehexylamide.

14. A pharmaceutical composition as claimed in claim 5 in unit dosage form for oral administration which comprises from 1 to 100 mg of said compound.

* * * * *